United States Patent [19]

Durr et al.

[11] Patent Number: 4,842,865

[45] Date of Patent: Jun. 27, 1989

[54] USE OF GLYCOFUROL FOR THE LIQUIDIZATION OF PHARMACEUTICAL PREPARATIONS TO BE FILLED INTO SOFT GELATINE CAPSULES

[75] Inventors: Manfred Durr, Pulheim/Dansweiler; Hans U. Fribolin, Neuss; Ekkerhard Harhausen, Sarkwitz; Jurgen Seidel, Pulheim, all of Fed. Rep. of Germany

[73] Assignee: A. Nattermann & CIE GmbH, Cologne, Fed. Rep. of Germany

[21] Appl. No.: 41,443

[22] Filed: Apr. 23, 1987

[30] Foreign Application Priority Data

Apr. 24, 1986 [DE] Fed. Rep. of Germany ....... 3613799

[51] Int. Cl.$^4$ ......................... B61K 9/64; B61K 37/22
[52] U.S. Cl. ..................................... 424/456; 424/450
[58] Field of Search ................ 260/403; 424/450, 451, 424/452, 455, 456

[56] References Cited

U.S. PATENT DOCUMENTS 2,483,748 10/1949 Wittcoff .
2,555,972 6/1951 Karjala et al. .
4,524,075 6/1975 Oduro-Yeboah .................. 514/451

FOREIGN PATENT DOCUMENTS 0056781 7/1982 European Pat. Off. ............ 424/450
0068044 4/1985 Japan .................................. 424/450

OTHER PUBLICATIONS

The Theory and Practice of Industrial Pharmacy; Dr. Leon Lachman, et al.; 1976; pp. 404–438; "Soft Gelatin Capsules".

*Primary Examiner*—Ferris H. Lander
*Attorney, Agent, or Firm*—Burns, Doane, Swecker & Mathis

[57] ABSTRACT

Use of glycofurol for the liquidization of pharmaceutical preparations containing more than 50% phosphatidyl choline with a high content of unsaturated fatty acids, which preparations can contain another active ingredient as well as phosphatidyl choline, and in which the viscosity so obtained permits filling into soft gelatine capsules.

7 Claims, No Drawings

USE OF GLYCOFUROL FOR THE LIQUIDIZATION OF PHARMACEUTICAL PREPARATIONS TO BE FILLED INTO SOFT GELATINE CAPSULES

DESCRIPTION

The substance of the present invention is the use of glycofurol to liquidize pharmaceutical preparations containing more than 50% phosphatidyl choline with a high content of unsaturated fatty acids, which preparations, apart from phosphatidyl choline, can contain another active ingredient, whereby the viscosity so reached permits filling into soft gelatine capsules. Together with other phospholipids, Phosphatidyl choline is a constituent of commercially available lecithins and is of particular importance because of its therapeutic application and its physiological application in nutrition.

The commercially available lecithin preparations contain 35 to a maximum of 55% w/w phospholipids together with vegetable oils and other conventional adjuvants; the phospholipids represent natural mixtures of various phospholipids such as phosphatidyl choline, phosphatidyl ethanolamine, phosphatidyl inositol etc. The preparations are taken as liquid mixtures or as granules. For therapeutic use however, preparations are desirable which contain a high content of pure phsphatidyl choline, as phosphatidyl choline has proved particularly useful in the treatment of disorders of fat metabolism, in diseases of the liver and in cerebral diseases. Of particular importance are phosphatidyl cholines with a high content of unsaturated and essential fatty acids, which can be represented by the following general formula:

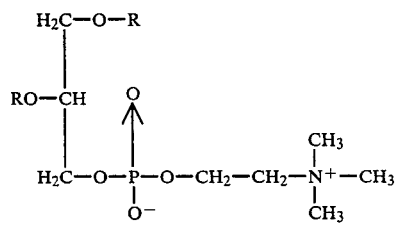

in which R=acyl residues of natural fatty acids such as palmitic acid, stearic acid, oleic acid, linoleic acid, linolenic acid and arachidonic acid, the unsaturated fatty acid content being over 70%. Now these phosphatidyl cholines are however plastic masses, which are difficult to process technically and difficult to manipulate and thus possess a considerable disadvantage in this state. For therapeutic application, the phosphatidyl choline must be converted to a state which makes possible a galenical preparation.

In choosing the form of presentation, the biological availability generally plays an important part; as a rule, solutions of an active ingredient possess better biological availability. Difficulties in the production of solutions often arise when the active ingredient is not water-soluble. In the choice of a suitable solvent, apart from adequate dissolving capacity, the physiological compatibility plays a particularly decisive role.

Converting phosphatidyl choline into an oral form of presentation necessitates a solvent which, apart from having good dissolving capacity and being physiologically harmless, produces solutions which are easy to process technically. In order to permit easy filling eg into soft gelatine capsules, the solutions may not exceed a certain viscosity.

The problem of the liquidization of phosphatides has been approached several times in the past. Thus in DE-PS No. 286 061 a process for the production of solutions with a high percentage of lecithin in oils and fats is described. As a solvent, a mixture of oleic acid and olive oil is used. A 40% lecithin solution is obtained. In another process (DE-AS No. 12 27 191) for the manufacture of liquid lecithin preparations polyalcohols (mannitol, arabitol, sorbitol) are used in conjunction with ethanol. The solutions obtained however have a maximum lecithin concentration of only 10%. U.S. Pat. No. 2,555,972 describes a phosphatide mixture of low viscosity, consisting of 50 to 60% phosphatides, 2 to 4% higher fatty acids, 30 to 47% vegetable oils and 1 to 6% propylene glycol. According to U.S. Pat. No. 2,483,748 phosphatides can also be liquefied with fatty acid esters such as soya oil fatty acid methyl ester and oleic acid ester among others. Phosphatide solutions of up to 80% phosphatide content are obtained, which are mobile at room temperature. All these processes are more or less suitable for the liquidization of commercially available lecithins. Commercially available lecithin however is a phosphatide mixture consisting of oil, phosphatidyl choline, phosphatidyl ethanolamine, phosphatidyl inositol and other accompanying lipids. The above mentioned processes begin with either this crude lecithin or de-oiled crude lecithin. In all cases the known processes deal with the liquidization of a crude phosphatide mixture. Crude phosphatide mixtures however have a different solution behaviour from their pure components. The solvents given in the known processes for the preparation of lecithin solutions cannot therefore be applied in the same manner to pure phosphatidyl choline.

In DE-PS No. 1141 639 phosphatidyl choline is made water-soluble by forming complexes with bile acids. The disadvantage however is that the ratio of phosphatidyl choline to bile acids is 1:1. In DE-OS No. 2556 592 also, liquid preparations of phosphatidyl choline, bile acids, sunflower oil and monoglycerides, wich can be filled into soft gelatine capsules, are described. The contents of phosphatidyl choline thus attained, however, are less than 20% w/w.

In DE-OS No. 2942849 highly concentrated phosphatidyl choline solutions are described in which lactic acid ethyl ester was used as a liquidizer. Lactic acid ethyl ester, however, is very unstable in the presence of small amounts of water, so that decomposition to lactic acid and ethyl alcohol occurs in the soft gelatine capsule; by lowering the pH value, the lactic acid causes decomposition of the fatty acids in the phosphatidyl choline, and unwanted lysophosphatidyl choline is formed. In addition, the ethyl alcohol simultaneously formed causes brittleness of the capsule shell.

As the manufacture of suitable phosphatidyl choline filling masses for soft gelatine capsules has been so unusually difficult, the use of hard gelatine capsules in place of soft gelatine capsules has been tried. In DE-OS No. 30 22 136, filling masses containing phosphatidyl choline are described, which are liquidized by the addition of triglycerides and ethyl alcohol, and the ethanol evaporates during filling. These masses however are not suitable for filling into soft gelatine capsules. For therapeutic application, however, soft gelatine capsules have proved of value because of their ease of manipulation, their ability to dissolve rapidyl after ingestion and their ability to offer better protection for the filled active ingredients, in particular against oxidation during long storage periods, especially in higher climatic regions.

The object of this invention was therefore to develop filling masses containing phosphatidyl choline for soft gelatine capsules, which masses contain more than 50% w/w phosphatidyl choline and which contain liquid substances that are compatible both with the active ingredient and with the capsule.

It was surprisingly found that filling masses having a high phosphatidyl choline content, for soft gelatine capsules, can be obtained if glycofurol is used as a liquidizing agent. Glycofurol (Tetrahydrofurylalcohol polyethylene glycol ether)

 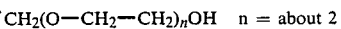 n = about 2 is a known solvent, is toxicologically harmless and has no pharamacodynamic activity of its own.

Considering the large number of dissolving agents which have already been applied, and of available liquidizing agents, it must be regarded as surprising that glycofurol should meet all the requirements for filling phsphatidyl choline into soft gelatine capsules.

Natural phosphatidyl cholines, derived from eg soya beans or egg, with a high content of unsaturated essential fatty acids, are used preferentially as phosphatidyl cholines. However other phosphatidyl cholines of natural or synthetic origin can also be used.

The phosphatidyl choline content of the filling mass is 50–94% w/w, preferably 70–79% w/w. For liquidizing it 5–20% w/w glycofurol, preferably 16–18% w/w, is added. To improve the working up, as much as 12% w/w natural oils, particularly soya oil, as much as 10% w/w 1,2-propandiol and 0.3–2% w/w ethanol can be added. If required, other conventional adjuvants such as antioxidants or flavouring substances can also be added. It is also possible to include other active ingredients in the processing.

Examples of further physiologically active substances which can be mixed in with the phosphatidyl choline are:

Plant extracts, eg Chelidonium, Crataegus, Curcuma, chestnut, Betula, grape extracts or senna extracts:
Fat-soluble or water-soluble vitamins, eg vitamin C, vitamin A, E, F, B-complexes or $B_{12}$;
Ethereal oils, eg those of fennel, caraway seeds, peppermint, eucalyptus;
Purines, eg theophyllin, theobromine or caffeine
Alkaloids, eg quinidine, ephedrine, codeine, atropine, papaverine, morphine, reserpine, strychnine, ergot alkaloids, especially ergotamine, ergocristine, ergocornine, raubasine, dihydroergotoxine, dihydroergotamine or dihydroergocristine;
Bile acids, eg desoxycholic acid or taurocholic acid
Saponins, eg aescine;
Hormones, eg methyltestosterone or ethinyl oestradiol
Sulphonamides or antibiotics, eg penicillin or cephalosporins:
Glycosides, eg cardiac glycosides, especially digoxin, digitoxin or strophantine:
Non-steroidal anti-rheumatics, eg acetylsalicylic acid, indomethacin, diclofenac or piroxicam
or other pharmaceutically relevant substances.

In the manufacture of the new filling mass, the phosphatidyl choline is comminuted, and brought into solution by the conventional method of stirring, in a mixture of alkandiol, eg propandiol or butandiol, and glycofurol, and, if required, a natural oil, and by heating to 70° C.

Ethanol may be subsequently added to adjust the viscosity as required. The phosphatidyl choline can also be dissolved in ethanol, and the the other solubilizing agents and auxiliary substances added thereto. Excess ethanol is afterwards drawn off. The active ingredients are worked homogeneously into this filling mass in a suitable mixer.

The filling masses thus obtained are filled into soft gelatine capsules according to processes known per se (see J. P. Stanley "Soft Gelatine Capsules" in "The theory and practice of indus pharm" editor L. Lachman, Publishers LEA & Febiger, Philadelphia 1976) such as eg the rotary die process and according to the commonly known filling conditions.

EXAMPLE 1

Manufacture of 5.36 Kg filling mass

| | |
|---|---|
| Phosphatidyl choline | 72% w/w |
| Glycofurol | 17% w/w |
| 1,2-Propandiol | 5% w/w |
| Soya oil | 5.5% w/w |
| Ethanol | 0.5% w/w |

The gelatinous phosphatidyl choline is comminuted and dissolved in the mixture of glycofurol, 1,2-propandiol and soya oil by stirring while heating to 70° C. The ethanol is then added.

The filling mass thus obtained is filled by the rotary die process into 8000 soft gelatine capsules of size 11 minims oblong. Filling weight per capsule 670 mg.

EXAMPLE 2

| | |
|---|---|
| Phosphatidyl choline | 79% w/w |
| Glycofurol | 17% w/w |
| Soya oil | 3% w/w |
| Ethanol | 1% w/w |

The phosphatidyl choline is dissolved in an excess of ethanol. The glycolfurol and the soya oil are then stirred in and the excess ethanol evaporated down to a content of 1% w/w in the complete mass.

The filling mass obtained is filled by the rotary die process into soft gelatine capsules of size 8 minims oblong.

Filling weight per capsule 500 mg.

EXAMPLE 3

| | |
|---|---|
| Phosphatidyl choline | 67% w/w |
| Glycofurol | 15% w/w |
| Soya oil | 12% w/w |
| 1,2-Propandiol | 5.7% w/w |
| Ethanol | 0.3% w/w |

Manufacture of the filling mass and filling into soft gelatine capsules are carried out as in example 1.

EXAMPLE 4

| Phosphatidyl choline | 72.5% w/w |
|---|---|
| Glycofurol | 20% w/w |
| Soya oil | 6.5% w/w |
| Ethanol | 1% w/w |

Manufacture of the filling mass and filling into soft gelatine capsules are carried out as in example 2.

EXAMPLE 5

| Phosphatidyl choline | 72.5% w/w |
|---|---|
| Glycofurol | 9.5% w/w |
| Soya oil | 11.5% w/w |
| 1,2-Propandiol | 5% w/w |
| Ethanol | 1.5% w/w |

Manufacture of the filling mass and filling into soft gelatine capsules are carried out as in example 2.

EXAMPLE 6

Phosphatidyl choline + active ingredient

Ingredients:
 3% Piroxicam
 70% Phosphatidyl choline
 16% Glycofurol
 5% Propandiol
 5.5% Soya oil
 0.5% Ethanol Manufacture:
Piroxicam is mixed homogeneously into the filling mass produced as in example 1, in a suitable mixer. Soft gelatine capsules of size 11 minims oblong with a filling weight of 670 mg were produced.

EXAMPLE 7

Phosphatidyl choline + active ingredient

Ingredients:
 5.0% Diclofenac sodium
 68.5% Phosphatidyl choline
 15.5% Glycofurol
 5.0% Propandiol
 5.5% Soya oil
 0.5% Ethanol Manufacture:
Diclofenac sodium is mixed homogeneously into the filling mass produced as in example 2, in a suitable mixer. Soft gelatine capsules of size 9 minims oblong with a filling weight of 500 mg were produced.

EXAMPLE 8

Phosphatidyl choline + active ingredient

Ingredients:
 7% Ethophyllin
 70% Phosphatidyl choline
 17% Glycofurol
 2% Propandiol
 3% Soya oil
 1% Ethanol Manufacture:
Ethophyllin is mixed homogeneously into the filling mass produced as in example 1. Soft gelatine capsules of size 11 minims oblong with a filling weight of 715 mg were produced.

EXAMPLE 9

Phosphatidyl choline + active ingredient

Ingredients:
 0.5% Dihydroergotamine methane sulfonate
 71.0% Phosphatidyl choline
 11.0% Glycofurol
 11.0% Propandiol
 5.0% Soya oil
 1.5% Ethanol Manufacture:
Phosphatidyl choline is dissolved in an excess of ethanol; a solution of dihydroergotamine methane sulfonate in glycofurol and propandiol is then added. After addition of the soya oil, the ethanol is distilled off down to the required value. Soft gelatine capsules of size 4 minims oval with a filling weight of 200 mg were produced.

EXAMPLE 10

Phosphatidyl choline + active ingredient

Ingredients:
 0.1% Digoxin
 77.0% Phosphatidyl choline
 15.0% Glycofurol
 3.0% Propandiol
 4.0% Soya oil
 0.9% Ethanol Manufacture:
As in example 9. Soft gelatine capsules of size 4 minims oval with a filling weight of 200 mg were produced.

What is claimed is:

1. Process for the liquidization of pharmaceutical preparations containing more than 50%, based on the total preparation, of phosphatidyl choline with a high content of unsaturated and essential fatty acids comprising combining said phosphatidyl choline with a glycofurol liquidizer in an amount effective to liquidize the phosphatidyl choline.

2. Process according to claim 1 further comprising filling the liquidized pharmaceutical preparation containing phosphatidyl choline into soft gelatine capsules.

3. Process according to claim 1 further comprising at least one of a vegetable oil and an alkanol as additional liquidizers, apart from glycofurol.

4. Process according to claim 3 wherein said pharmaceutical preparation contains 50 to 94% phosphatidyl choline, 2 to 20% glycofurol, 0 to 12% soya oil, 0 to 10% 1,2-propandiol and 0.3 to 2% ethanol.

5. Process according to claim 4 wherein said pharmaceutical preparation contains 70 to 79% phosphatidyl choline, 16 to 18% glycofurol, 4 to 6% soya oil, 4 to 5.5% 1,2-propandiol and 0.5 to 1% ethanol.

6. Process according to claim 1 wherein said pharmaceutical preparation is charged with 0.1 to 10% of a physiologically active substance.

7. Process according to claim 1 wherein said pharmaceutical preparation contains 70 to 94% phosphatidyl choline.

* * * * *